(12) United States Patent
Ko et al.

(10) Patent No.: US 12,727,803 B2
(45) Date of Patent: Sep. 8, 2026

(54) EARLY ASSISTIVE DIAGNOSIS SYSTEM OF ADHD

(71) Applicant: National Yang Ming Chiao Tung University, Hsinchu City (TW)

(72) Inventors: Li-Wei Ko, Hsinchu City (TW); I-Chun Chen, Taipei City (TW); I-Wen Huang, Miaoli City (TW); Jo-Wei Lin, Taichung City (TW); Zuo-Cian Fan, Guanxi Township (TW); Chih-Hao Chang, Taoyuan City (TW); Yang Chang, Taichung City (TW)

(73) Assignee: NATIONAL YANG MING CHIAO TUNG UNIVERSITY, Hsinchu City (TW)

( * ) Notice: Subject to any disclaimer, the term of this patent is extended or adjusted under 35 U.S.C. 154(b) by 369 days.

(21) Appl. No.: 18/531,895

(22) Filed: Dec. 7, 2023

(65) Prior Publication Data

US 2024/0188866 A1 Jun. 13, 2024

(30) Foreign Application Priority Data

Dec. 8, 2022 (TW) ................................ 111147134

(51) Int. Cl.
*A61B 5/00* (2006.01)
*A61B 5/16* (2006.01)
(Continued)

(52) U.S. Cl.
CPC .............. *A61B 5/168* (2013.01); *A61B 5/291* (2021.01); *A61B 5/372* (2021.01); *A61B 5/378* (2021.01);
(Continued)

(58) Field of Classification Search
CPC ......... A61B 5/168; A61B 5/291; A61B 5/372; A61B 5/378; A61B 5/38; A61B 5/6814;
(Continued)

(56) References Cited

U.S. PATENT DOCUMENTS

| | | | | |
|---|---|---|---|---|
| 8,473,043 B1 * | 6/2013 | Modarres | ............ | A61B 5/4848 600/544 |
| 12,070,337 B2 * | 8/2024 | Jin | ...................... | A61B 5/4088 |

(Continued)

FOREIGN PATENT DOCUMENTS

| | | | |
|---|---|---|---|
| KR | 20140077694 A * | 6/2014 | ............ A61B 5/168 |
| TW | 202007360 A | 2/2020 | |

(Continued)

OTHER PUBLICATIONS

Chen et al., "EEG characteristics of children with attention-deficit/hyperactivity disorder," Neuroscience, vol. 406, 2019, pp. 444-456.

*Primary Examiner* — May A Abouelela
(74) *Attorney, Agent, or Firm* — Birch, Stewart, Kolasch & Birch, LLP

(57) ABSTRACT

An early assistive diagnosis system of ADHD provides a test to the subject and uses a brain-computer interface (BCI) to detect the electroencephalography (EEG) signals of subject. A host receives the EEG signals, captures the features associated with ADHD heterogeneities, obtains feature EEG signals, and classifies the subject as typical development or ADHD, then uses the EEG feature signals to train a predicted index score range for the heterogeneities of ADHD. The test scores of a new subject is tested, it is compared whether the scores fall within the predicted index score range to determine the ADHD heterogeneity types to which the new subject belongs. Thus, the present invention uses attention tests for ADHD in combination with EEG signals to assess symptoms of a subject, further predicts the poten-
(Continued)

tial aptitude of a subject for ADHD and provides objective assistive diagnosis to physicians.

8 Claims, 5 Drawing Sheets

(51) Int. Cl.
*A61B 5/291* (2021.01)
*A61B 5/372* (2021.01)
*A61B 5/378* (2021.01)
*A61B 5/38* (2021.01)

(52) U.S. Cl.
CPC .............. *A61B 5/38* (2021.01); *A61B 5/6814* (2013.01); *A61B 5/7207* (2013.01); *A61B 5/725* (2013.01); *A61B 5/7253* (2013.01); *A61B 5/7267* (2013.01); *A61B 2560/0468* (2013.01); *A61B 2560/0487* (2013.01)

(58) Field of Classification Search
CPC ..... A61B 5/7207; A61B 5/725; A61B 5/7253; A61B 5/7267; A61B 2560/0468; A61B 2560/0487; A61B 5/165; A61B 5/369; A61B 5/7264; A61B 5/374
See application file for complete search history.

(56) References Cited

U.S. PATENT DOCUMENTS

2003/0013981 A1* 1/2003 Gevins ................ A61B 5/4076 600/544
2003/0120172 A1* 6/2003 Foust ..................... A61B 5/168 600/549
2004/0243328 A1* 12/2004 Rapp .................... A61B 5/7264 702/71
2005/0131292 A1* 6/2005 Huss ..................... A61B 5/1118 600/430
2008/0167571 A1* 7/2008 Gevins ................... A61B 5/377 600/544
2008/0269632 A1* 10/2008 Snyder ................... A61B 5/168 600/544
2009/0149770 A1* 6/2009 Sing ......................... A61B 5/18 600/544
2009/0287107 A1* 11/2009 Beck-Nielsen .......... A61B 5/37 600/544
2011/0066065 A1 3/2011 Snyder
2011/0191350 A1* 8/2011 Zhang .................. A61B 5/7267 707/743
2011/0270117 A1* 11/2011 Warwick ............. A61B 5/0006 600/544
2012/0046569 A1* 2/2012 Johnstone ................ A61B 5/16 434/247
2012/0221075 A1* 8/2012 Bentwich ............... G16H 20/70 607/45
2012/0296569 A1* 11/2012 Shahaf ................... A61B 5/383 702/19
2013/0060125 A1* 3/2013 Zeman ................... A61B 5/374 600/409
2014/0107521 A1* 4/2014 Galan ................. A61B 5/4088 600/544
2015/0073294 A1* 3/2015 Zhang .................... A61B 5/168 600/544
2015/0105837 A1* 4/2015 Aguilar Domingo . A61B 5/374 607/45
2015/0112153 A1* 4/2015 Nahum .................... A61B 5/11 600/383
2015/0157235 A1* 6/2015 Jelen ...................... A61B 5/291 600/383
2015/0199010 A1* 7/2015 Coleman ................ A61B 5/369 345/156
2015/0305686 A1* 10/2015 Coleman ............. A61B 5/7264 600/301
2015/0351655 A1* 12/2015 Coleman ............. A61B 5/0205 600/595
2016/0038049 A1* 2/2016 Geva ................. A61N 1/36135 600/300
2016/0220166 A1* 8/2016 Thornton ............... A61B 5/316
2016/0287157 A1* 10/2016 Simpson ............. A61B 5/6814
2017/0229037 A1* 8/2017 Gazzaley ............ A61B 5/4088
2018/0092557 A1* 4/2018 Bickford ............. A61B 5/0059
2018/0154104 A1* 6/2018 Gerdes ................ A61B 5/6814
2018/0184937 A1* 7/2018 Kaddan ................ A61B 5/7267
2018/0220957 A1* 8/2018 Fuerst .................... G16H 40/67
2018/0221620 A1* 8/2018 Metzger ................... A61B 5/38
2018/0228394 A1* 8/2018 Tansey ................... A61B 5/369
2018/0286272 A1* 10/2018 Mcdermott ............ A63F 13/46
2018/0360376 A1* 12/2018 Garcia Molina .... A61B 5/4812
2019/0216389 A1* 7/2019 Scheib ................... A61B 5/743
2019/0216392 A1* 7/2019 Bower ................... G16H 30/40
2019/0247654 A1* 8/2019 Alyagon .............. A61B 5/4076
2020/0155053 A1* 5/2020 Bernstein ............... A61B 5/163
2020/0174557 A1* 6/2020 Alailima ................ G16H 40/63
2020/0237247 A1* 7/2020 Glik ....................... A61B 5/369
2020/0380882 A1* 12/2020 Alailima ............. A61B 5/4836
2021/0128917 A1* 5/2021 Phillips .................. A61N 2/006
2021/0169417 A1* 6/2021 Burton ................. A61B 5/4857
2021/0353957 A1* 11/2021 Telfer ................... A61B 5/4064
2022/0101981 A1* 3/2022 Kovacevic ............. A61B 5/374
2022/0211325 A1* 7/2022 Malish ................... A61N 2/006
2024/0108272 A1* 4/2024 Hendler ................. A61B 5/372
2024/0221950 A1* 7/2024 Kollada ............... A61B 5/0205
2024/0285222 A1* 8/2024 Rothenberg ......... A61B 5/4827
2024/0366140 A1* 11/2024 Adamos ................. G16H 20/70
2024/0411368 A1* 12/2024 Lidsky .................... G06F 3/015

FOREIGN PATENT DOCUMENTS

WO WO-2011025953 A1 * 3/2011 ............. A61B 5/374
WO WO-2014138925 A1 * 9/2014 ............. G16H 40/67
WO WO-2015109368 A1 * 7/2015 .......... A61B 5/7275

* cited by examiner

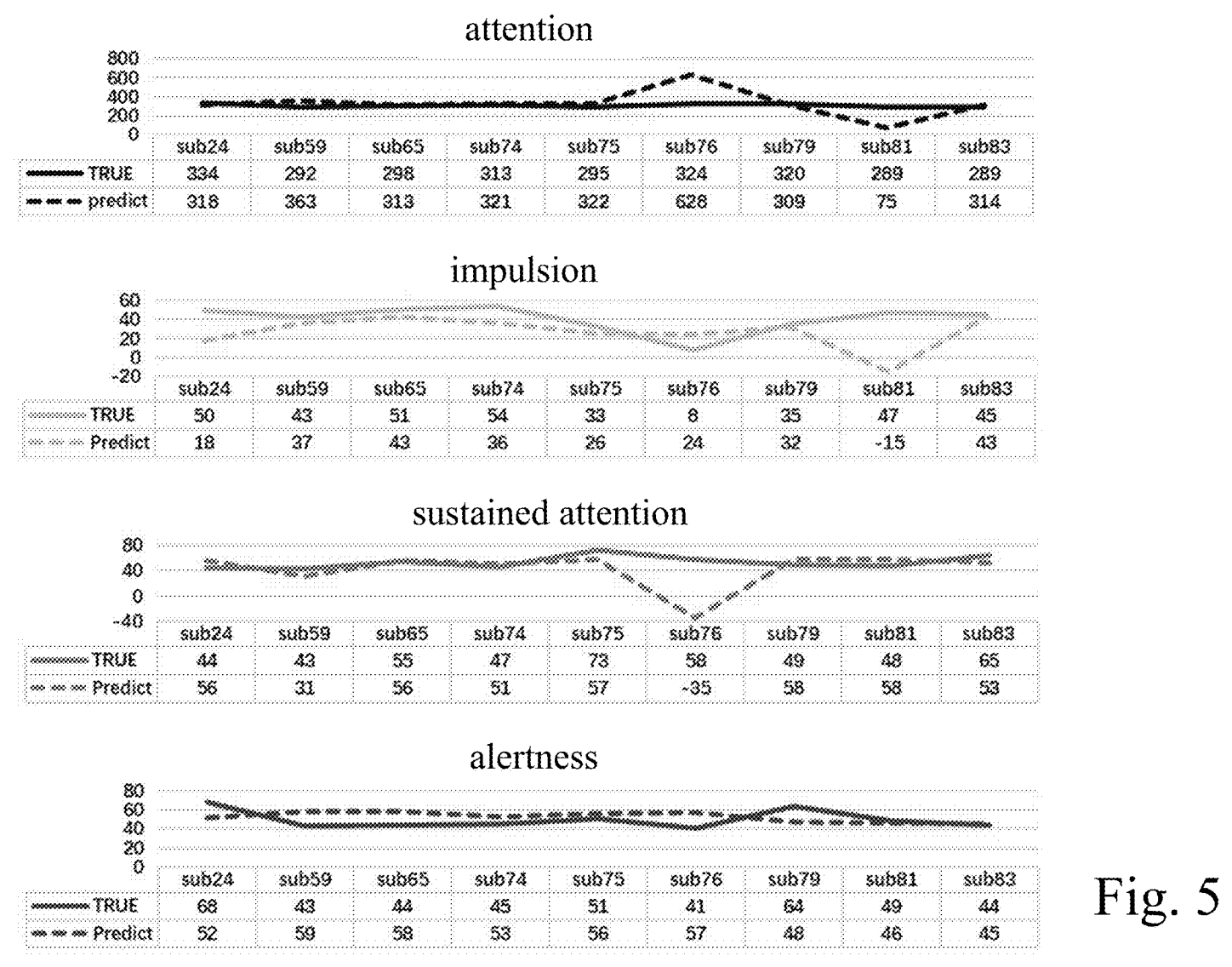

| | sub24 | sub59 | sub65 | sub74 | sub75 | sub76 | sub79 | sub81 | sub83 |
|---|---|---|---|---|---|---|---|---|---|
| TRUE | 334 | 292 | 298 | 313 | 295 | 324 | 320 | 269 | 289 |
| predict | 318 | 363 | 313 | 321 | 322 | 628 | 309 | 75 | 314 |

| | sub24 | sub59 | sub65 | sub74 | sub75 | sub76 | sub79 | sub81 | sub83 |
|---|---|---|---|---|---|---|---|---|---|
| TRUE | 50 | 43 | 51 | 54 | 33 | 8 | 35 | 47 | 45 |
| Predict | 18 | 37 | 43 | 36 | 26 | 24 | 32 | -15 | 43 |

| | sub24 | sub59 | sub65 | sub74 | sub75 | sub76 | sub79 | sub81 | sub83 |
|---|---|---|---|---|---|---|---|---|---|
| TRUE | 44 | 43 | 55 | 47 | 73 | 58 | 49 | 48 | 65 |
| Predict | 56 | 31 | 56 | 51 | 57 | -35 | 58 | 58 | 53 |

| | sub24 | sub59 | sub65 | sub74 | sub75 | sub76 | sub79 | sub81 | sub83 |
|---|---|---|---|---|---|---|---|---|---|
| TRUE | 68 | 43 | 44 | 45 | 51 | 41 | 64 | 49 | 44 |
| Predict | 52 | 59 | 58 | 53 | 56 | 57 | 48 | 46 | 45 |

Fig. 5

EARLY ASSISTIVE DIAGNOSIS SYSTEM OF ADHD

BACKGROUND OF THE INVENTION

This application claims priority for the TW patent application no. 111147134 filed on 8 Dec. 2022, the content of which is incorporated by reference in its entirely.

FIELD OF THE INVENTION

The present invention relates to an Electroencephalogram (EEG) detection system, particularly to the early assistive diagnosis system of ADHD.

DESCRIPTION OF THE PRIOR ART

Attention Deficit Hyperactivity Disorder (ADHD) is diagnosed by doctors through interviews, behavioral observations, interactions during games, measuring scales and questionnaires. Validated and standardized assessment scales are completed by parents and teachers based on long-term observations in multiple contexts but may be less reliable due to the features, parental misjudgment of behavioral development, or differences in environmental structure. As such, it is essential for clinicians to use a scientific and impartial approach to diagnose ADHD.

At present, a technology utilizes electroencephalographic (EEG) signals to identify EEG signals of ADHD, but it does not collect data from the resting state or during task execution of brain for machine learning. As a result, it cannot compare resting and task-state EEG, nor is there a benchmark for comparison. Another method is to utilize EEG data for detecting ADHD, which can identify the ADHD subtypes with greater complexity. Nevertheless, this method can only differentiate between ADHD subtypes and cannot distinguish the varying features of subtypes at a detailed level.

In light of the aforementioned limitations of current techniques and future demands, an early assistive diagnosis system of ADHD is proposed by the present invention. The aim is to address these deficiencies, and the specific framework and implementation method will be outlined in the forthcoming sections.

SUMMARY OF THE INVENTION

The primary objective of the present invention is to provide an early assistive diagnosis system of ADHD. This system mechanically learns and categorizes the EEG signals of patients. It then calculates predicted index scores using test scores produced from tests and brain porter symptom data. This process assists in distinguishing between various types of ADHD and providing more compelling test results.

Another objective of the present invention is to provide an auxiliary diagnostic system for early detection of ADHD. The system records the resting-state EEG signals and task-state EEG signals of the subject during the test. It then classifies these signals to determine whether the subject is normal or not. The data of an individual is collected as a benchmark for comparison with the ADHD patient. The objective of this system is to use these results to diagnose ADHD at an earlier stage.

To achieve the abovementioned objectives, the present invention provides an early assistive diagnosis system of ADHD. which comprises: an attention testing device providing a test to a subject; a brain-computer interface (BCI), including a plurality of electrodes arranged on the scalp of the subject to detect a plurality of electroencephalography (EEG) signals of the subject, wherein the EEG signals includes resting-state EEG signals detected during rest and task-state EEG signals during the test; and a host, which connects to the attention testing device and the BCI, receive and analyze the EEG signals detected by the BCI, wherein the host includes: a controller connected to the attention testing device receives and generates a plurality of test scores of the test; a feature acquisition processor connected to the controller and the BCI acquires a plurality of ADHD-related features of the EEG signals of the frequency band power of each channel on the electrodes and band ratio thereof, so as to obtain EEG feature data; and a feature analysis processor connected to the feature acquisition processor receives the EEG feature data, classifies the subject as typical development group or ADHD group according to the EEG feature data, and if the subject is classified as ADHD, the feature analysis processor combines the EEG feature data and the test scores corresponding to the subject to produce predicted index score ranges of a plurality of ADHD heterogeneity types.

According to one embodiment of the present invention, the electrodes of the BCI include multiple channels respectively having different frequency band power.

According to an embodiment of the present invention, the host further includes a first filter which connected with the BCI and the feature acquisition processor. The first filter receives EEG signals, removes environmental artifacts in the EEG signals, and preserves the primary frequency range of EEG.

According to an embodiment of the present invention, the host further includes a second filter connected to the BCI and the feature acquisition processor. The second filter removes the artifacts originating from eye or muscle movements within the EEG signals using an artificial intelligence algorithm.

According to an embodiment of the present invention, the host further includes a time-frequency converter connected to the BCI and the feature acquisition processor. The time-frequency converter transforms time-domain signals of the resting-state EEG signals and the task-state EEG signals into frequency-domain signals, and then calculates the frequency band power of the frequency bands of each channel separately.

According to an embodiment of the present invention, the feature analysis processor uses a machine learning algorithm to classify the subject.

According to an embodiment of the present invention, the feature analysis processor uses machine learning algorithms to compute the ADHD heterogeneity types of the subject.

According to an embodiment of the present invention, the machine learning algorithm is a regression analysis.

According to an embodiment of the present invention, the ADHD heterogeneity types include problems of attention, impulsivity, sustained attention, and vigilance.

According to an embodiment of the present invention, the attention testing device is a computer that administers a game or video to provide visual or auditory stimulation to the subject. This facilitates objective measurement of attention levels, free from personal bias or opinion. The text is concise to ensure brevity and clarity, and the language adheres to standardized units and spellings.

According to an embodiment of the present invention, when a new subject is tested and the EEG signals are measured, the feature acquisition processor obtains the EEG data of the new subject to predict an index score, and determines the ADHD heterogeneity type of the new subject belongs by comparing whether the index score of the new subject falls within the predicted index score range.

BRIEF DESCRIPTION OF THE DRAWINGS

FIG. 5 shows the curves of the experimental results of the heterogeneities of ADHD of children.

DETAILED DESCRIPTION OF THE INVENTION

Technical solutions for the present invention will be described clearly and completely in connection with the accompanying figures. It should be noted that these embodiments are only a portion of the present invention and not all of them. Jargon and complex sentences are minimized throughout the document, ensuring clarity and coherence. The tone is neutral and formal while maintaining consistency in specific terms, abbreviations and units. The language is unambiguous and precise, following a logical structure enhanced with bulleted lists and headings. Sequential logic is applied to descriptions of processes to ensure ease of comprehension. Active voice is predominantly used for a better, direct communication style. The document is free from all grammatical errors and redundant fillers while adhering to industry-specific standardized language and precise word choice. Based on the embodiments of the present invention, all other embodiments achieved by a skilled individual without the need for an inventive effort fall within the scope of protection of the present invention.

Reference throughout this specification to "one embodiment" or "an embodiment" means that a particular feature, structure, or features described in connection with the embodiment is included in at least one embodiment. Thus, the appearances of the phrases "in one embodiment" or "in an embodiment" in various places throughout this specification are not necessarily all referring to the same embodiment.

Unless otherwise specified, some conditional sentences or words, such as "can", "could", "might", or "may", usually attempt to express what the embodiment in the present invention has, but it can also be interpreted as a feature, element, or step that may not be needed. In other embodiments, these features, elements, or steps may not be required.

The embodiments described below are illustrated to demonstrate the technical contents and features of the present invention and to enable the persons skilled in the art to understand, make, and use the present invention. However, it shall be noticed that, it is not intended to limit the scope of the present invention. Therefore, any equivalent modification or variation according to the spirit of the present invention is to be also included within the scope of the present invention.

Figure 1:
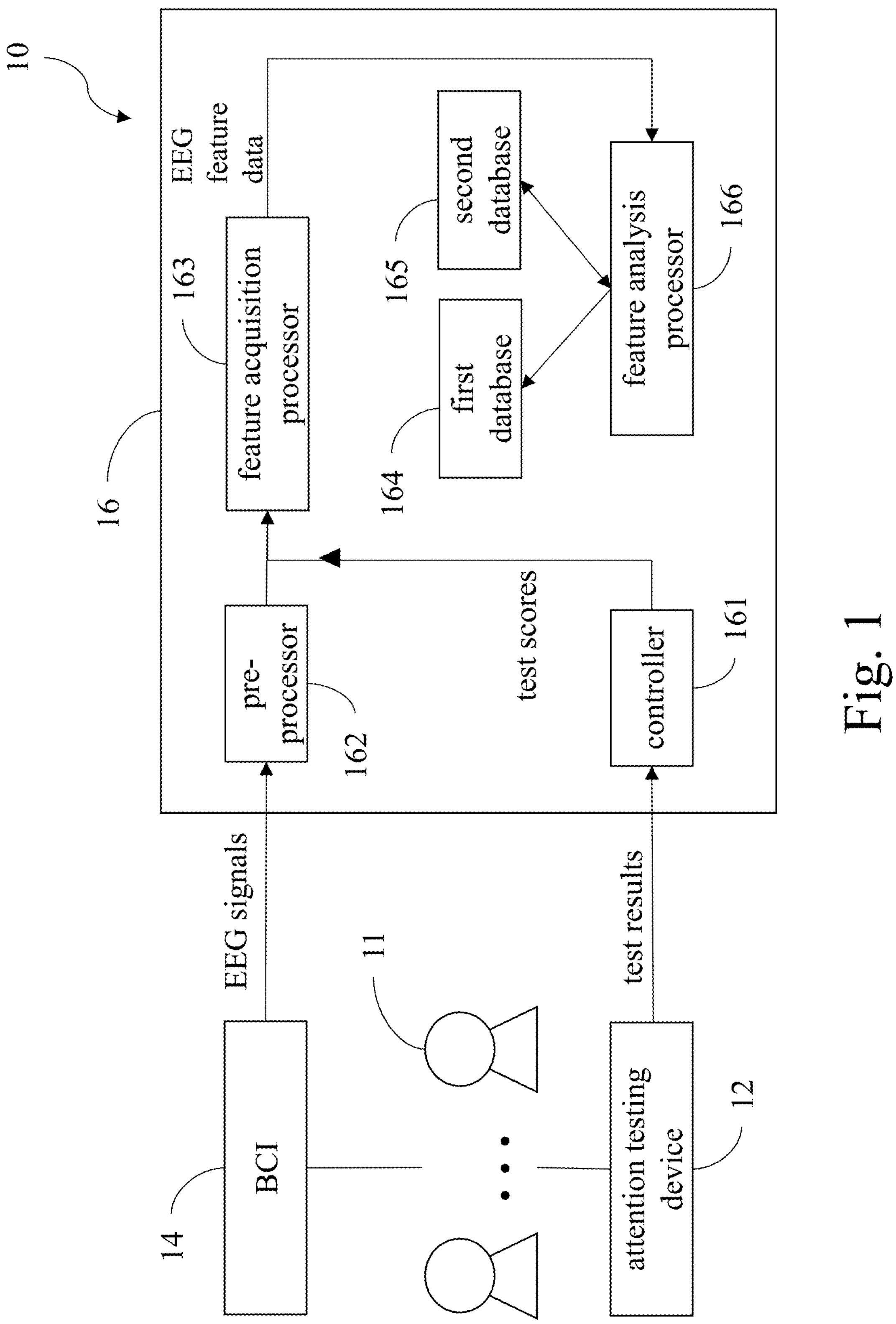
FIG. 1 is a block diagram of an early assistive diagnosis system of ADHD according to one embodiment of the present invention.

The present invention provides an early assistive diagnosis system of ADHD, please refer to FIG. 1, which is a block diagram of the early assistive diagnosis system of ADHD 10 of the present invention. The early assistive diagnosis system of ADHD 10 comprises an attention testing device 12, a brain-computer interface (BCI) 14, and a host 16. The attention testing device 12 is a computer with a display screen that provides a subject 11 with a game or video that causes a visual or auditory stimulus to perform a test. In some embodiments, the test is a game specifically designed to give the subject 11 an attention test, such as KCPT (an attention test software for children aged 4 to 7 years) and CPT (an attention test software for children aged 8 to 16 years), etc., which generates 9 standardized test scores. The BCI 14 configured on the head of the subject 11 can use electrodes (not shown) to detect EEG signals of the subject 11, including resting-state EEG signals in a resting state and task-state EEG signals during the test. In some embodiments, the BCI 14 is an EEG cap worn on the head of the subject 11. Each electrode of the BCI 14 comprises channels, each channel having a different band power.

The host 16 is connected to an attention testing device 12 and a BCI 14 to receive test results from the attention testing device 12 and EEG signals detected by the BCI 14. The host 16 includes a controller 161, at least one pre-processor 162, a feature acquisition processor 163, a first database 164, a second database 165, and a feature analysis processor 166. The abovementioned complex processors are capable of analyzing the test results and the EEG signals.

The controller 161 is connected to the attention testing device 12, and the test results after the subject 11 completes the test are transmitted to the controller 161, which calculates a set of test scores. In the case of the KCPT attention test software, for example, nine test scores are generated. These test scores are used to train a prediction model, and once the prediction model is trained, the EEG signals of new subjects can be analyzed directly using the prediction model, without the use of test scores. The method of generating the prediction model is described below.

Figure 2:
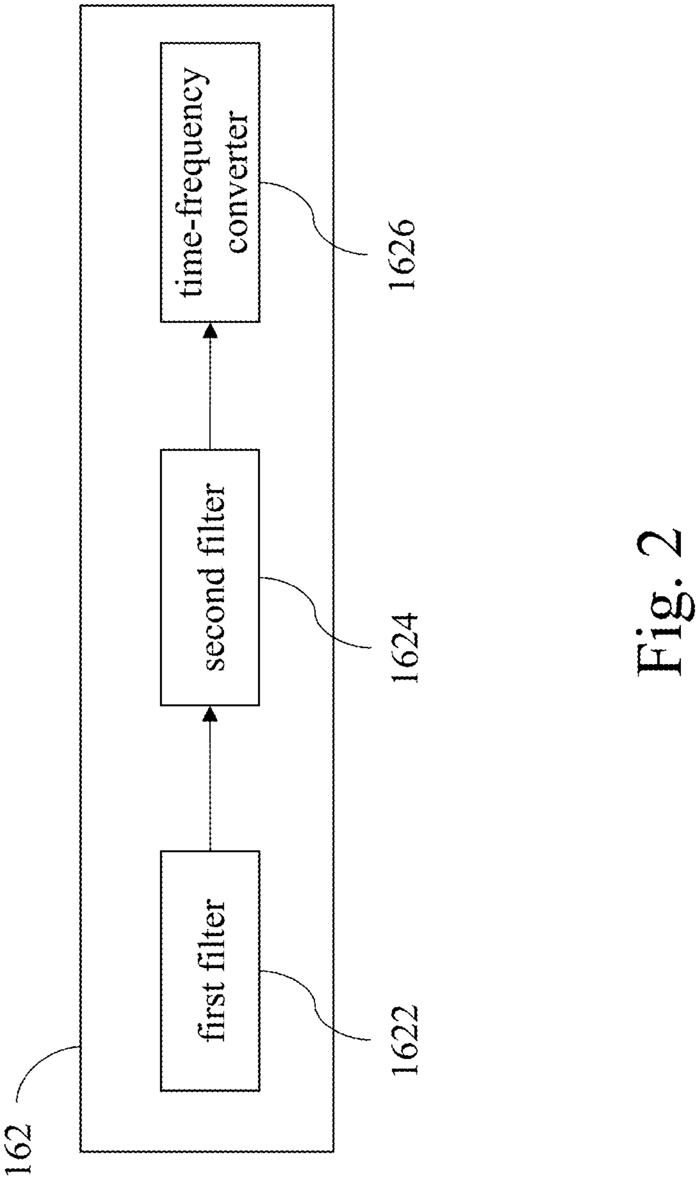
FIG. 2 is a block diagram of the pre-processor of an early assistive diagnosis system of ADHD according to one embodiment of the present invention.

The pre-processor 162 filters artifacts and converts the time and frequency domains of EEG signals. Please refer to FIG. 2, a block diagram of the pre-processor 162. The pre-processor 162 includes a first filter 1622, a second filter 1624, and a time-frequency converter 1626. The first filter 1622 and the second filter 1624 may both exist or only one. When both the first filter 1622 and second filter 1624 are present simultaneously, they are connected as illustrated in FIG. 2. The first filter 1622 is directly connected to the BCI 14 and the second filter 1624, and indirectly linked to the feature acquisition processor 163. The second filter 1624 is connected to the first filter 1622 and the time-frequency converter 1626, and indirectly connected to both the BCI 14 and the feature acquisition processor 163. The time-frequency converter 1626 is linked to the second filter 1624 and the feature acquisition processor 163, and is indirectly linked to the BCI 14. The first filter 1622 is a bandpass filter that receives the EEG signals from the BCI 14, removes environmental artifacts from the EEG signals, and retains the primary frequency range of the EEG. For instance, to obtain a cleaner EEG signal, we remove environmental artifacts that exceeds 50 Hz and non-brain components. The second filter 1624 removes artifacts created by eye or muscle movements in the EEG signal by integrating a processing unit (not visible in the diagram) into it to remove artifacts with the use of artificial intelligence. The time-frequency converter 1626 transforms the resting-state EEG signals and task-state EEG signals from the time-domain into frequency-domain signals using a fast Fourier transformation. To obtain frequency domain information, the power of each channel of BCI 14 is calculated for δ (1-4 Hz), θ (5-8 Hz), α (9-12 Hz), and β (13-30 Hz) channels, respectively.

The feature acquisition processor 163 is linked to the controller 161 and the pre-processor 162, and is indirectly linked to the BCI 14. Upon receipt of the test scores from controller 161 and clean EEG signals from pre-processor 163, feature acquisition processor 163 obtains complex ADHD-related features by assessing the frequency band power of each channel of BCI 14, as well as its band ratios θ/β and θ/α. These features are then utilized to acquire complex EEG features. These EEG signals can effectively predict and analyze the likelihood of ADHD and typical development.

The feature analysis processor 166 connects to the feature acquisition processor 163 to receive the EEG feature data captured by the latter. The operation of the feature analysis processor 166 is divided into two stages. In the first stage, the subject is classified based on the EEG feature data to determine if they exhibit typical development behavior or symptoms of ADHD. In the initial phase, feature analysis processor 166 partitioned the exam data for each participant (consisting of EEG signals, EEG feature data, test scores, among others) into a predetermined ratio of training and validation data. Next, the training and validation data sets were merged, and finally, the subjects were classified through a machine learning algorithm. The information pertaining to the subjects categorized as typical development is stored in the initial database 164, whereas the data corresponding to the subjects diagnosed with ADHD is saved in the second repository 165.

In the second stage, the feature analysis processor 166 retrieves from the second database 165 the EEG feature data of the subjects classified as whether they have ADHD. The feature analysis processor 166 combines the test scores generated after the test and the EEG feature data of the subjects and then uses a machine-learning algorithm (such as a regression analysis technology) to train the predicted index scores corresponding to different heterogeneities in ADHD. The predicted index scores respectively distribute in different ranges. Suppose that a new subject receives the test and the EEG measurement and that the index score, which is predicted using the EEG feature data, falls into the range of the predicted index scores. It indicates that the new subject has features of an ADHD heterogeneity type. The ADHD heterogeneity types include the problems of attention, impulsivity, sustained attention, and vigilance.

Figure 3:
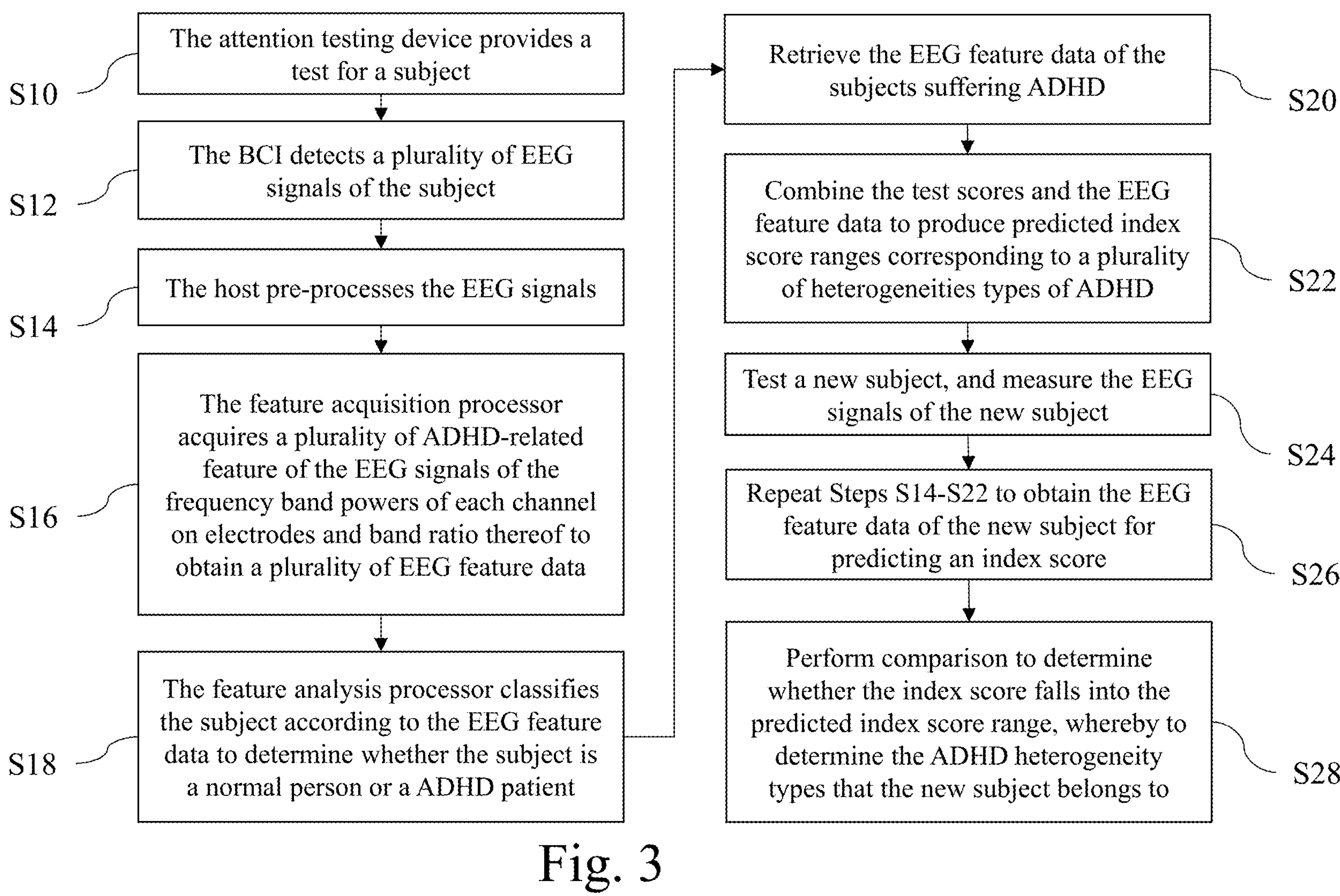
FIG. 3 is a flowchart of the process of using the early assistive diagnosis system of ADHD according to one embodiment of the present invention.

Refer to FIG. 3 for a flowchart of the process of using the early assistive diagnosis system of ADHD 10 according to one embodiment of the present invention. In Step S10, the attention testing device 12 provides a test for a subject 11; after the subject 11 completes the test, the attention testing device 12 generates a test result. In Step S12, the BCI 14 is used to detect EEG signals of the subject 11. The EEG signals include resting-state EEG signals of the subject 11 during rest and task-state EEG signals of the subject 11 during test. In Step S14, the host 16 receives the test scores output by attention testing device 12 and the EEG signals output by the BCI 14, wherein the controller 161 generates the test scores according to the test result; the pre-processor 162 pre-processes the EEG signals, including filtering out artifacts and transforming time-domain signals to frequency-domain signals. In Step S16, the feature extract processor 163 of the host 16 extracts ADHD-related features from the EEG signals of the frequency band powers and the frequency band power ratios of each channel to obtain EEG feature data. In Step S18, the feature analysis processor 166 of the host 16 classifies the subject 11 according to the EEG feature data to determine whether the subject is a typical development person or ADHD patient. In detail, the feature analysis processor 166 divides the test data of all the subjects 11 into training data and verification data and then uses a machine-learning algorithm to recognize the typical development subjects and subjects suffering ADHD. In Step S20, the feature analysis processor 166 retrieves the EEG feature data of the subjects 11 suffering ADHD. In Step S22, the feature analysis processor 166 combines the test scores and the EEG feature data of the subjects 11 suffering ADHD and uses a machine-learning technology to train a predicted model, whereby to obtain the range of the predicted index scores corresponding to heterogeneities of ADHD. After the predicted model has been established, the process proceeds to Steps S24-S28. A new subject is tested, and the EEG signals of the new subject are measured to obtain the EEG features of the new subject and determine whether the new subject is a typical development person or a patient suffering ADHD according to the abovementioned Steps S14-S18. If the new subject is a patient suffering ADHD, the EEG features are used to predict an index score according to the abovementioned Steps S20-S22, and it is determined whether the index score falls into the range of predicted index scores, whereby to determine the ADHD heterogeneity types that the new subject belongs to.

Figures 4A, 4B:
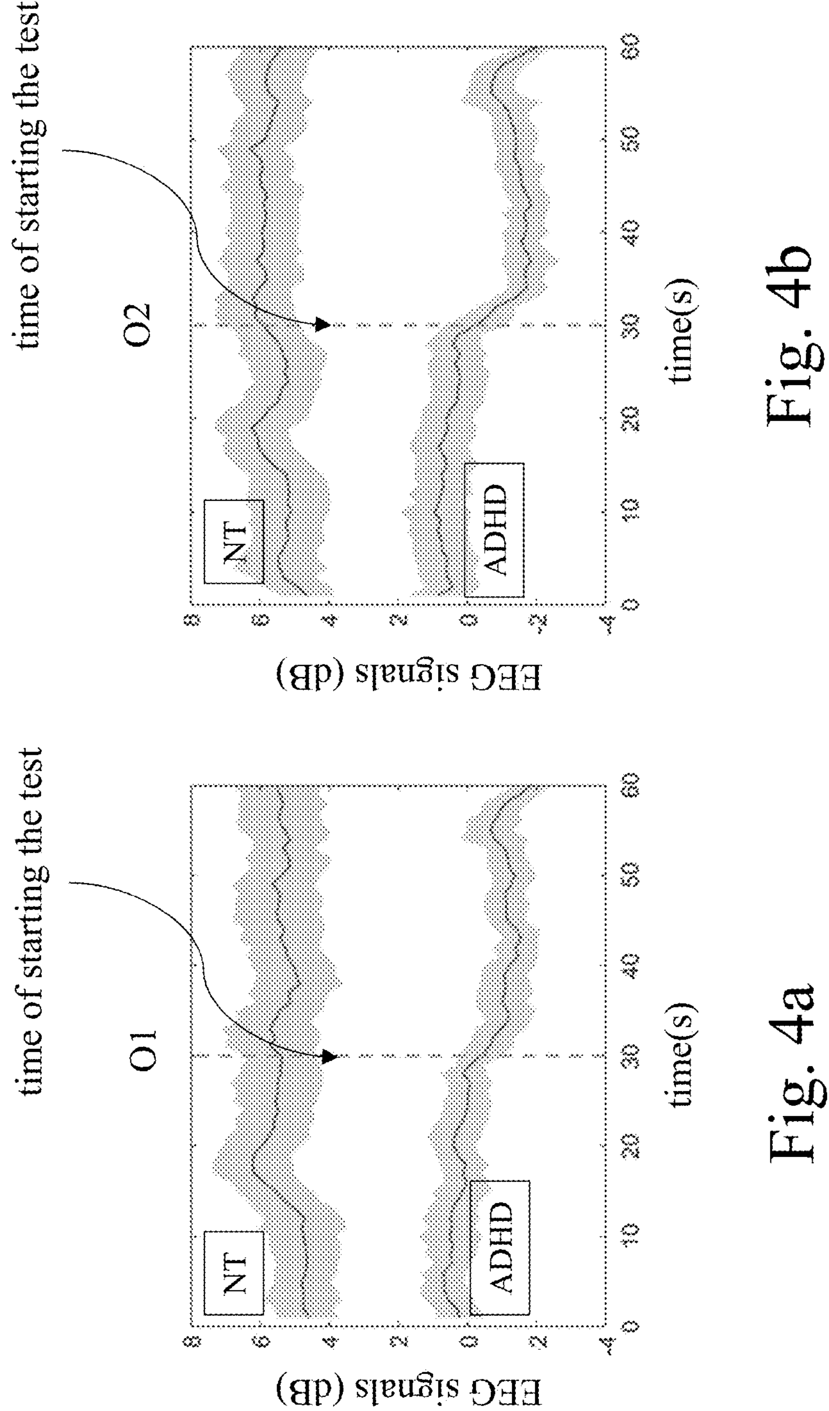
FIG. 4*a* and FIG. 4*b* respectively show the time-dependent variations of the β EEGs of the left occipital lobe (O1) and the right occipital lobe (O2) of the development group and the ADHD group.

In the abovementioned first stage, the present invention uses the machine-learning technology to recognize the typical development children and the children suffering ADHD. Refer to FIG. 4*a* and FIG. 4*b*, which show respectively the time-dependent variations of the ß EEGs of the left occipital lobe (O1) and the right occipital lobe (O2) from the resting state to the active (testing) state (such as during the test CPT). In FIG. 4*a* and FIG. 4*b*, the upper curves (NT) represent the EEG signals of the typical development group, and the lower curves (ADHD) represent the EEG signals of the patients suffering ADHD. The dashed lines in the middle represent the time of starting the test. The part on the left of the dashed line is the EEG of the resting state; the part in the right of the dashed line is the EEG of the active state. It is observed from FIG. 4*a* and FIG. 4*b*: the EEG of the ADHD group is lower that the EEG of the typical development group, especially during the test. Therefore, the EEG diagrams can be used to recognize the typical development group and the ADHD group effectively.

In the abovementioned second stage, the present invention can further predict four heterogeneity scores of the ADHD children. The parameters of the heterogeneity scores need to refer to the test scores obtained in the cognition test. There are 9 standardized scores in the common clinical CPT test as shown in Table I below.

TABLE I

Indexes of CPT 9 standardized scores

| Category | Item | Statement | Classification | Heterogeneity |
|---|---|---|---|---|
| Detectability | d' | Ability to discriminate targets from non-targets | Less ability to discriminate targets from non-targets (raw scores can be negative, indicating greater ability) | Attention |
| Error | Omissions | Rate of | Greater rate | Attention |

TABLE I-continued

| Indexes of CPT 9 standardized scores | | | | |
|---|---|---|---|---|
| Category | Item | Statement | Classification | Hetero-geneity |
| Type | | missing targets | of omission errors | |
| | Commissions | Rate of incorrect responses | Greater rate of commission errors | Attention/hyper-activity |
| | Perseverations | Rate of anticipatory, repetitive, or random responses | Greater rate of perseverative errors | Hyper-activity |
| Reaction Time Statistics | Hit Reaction Time (HRT) | Average response speed | Slower response speeds | Attention/hyper-activity |
| | Hit Reaction Time Standard Deviation (HRT SD) | Average response speed | Less consistent response speeds | Attention |
| | Variability | Variability of response speed consistency | Higher variability of response speeds across sub-blocks | Attention |
| | Hit Reaction Time Block Change (HRT Block Change) | Change in HRT across blocks | Slower response speeds in the later blocks | N/A |
| | Hit Reaction Time Inter-Stimulus Interval Change (HRT ISI Change) | Change in HRT across ISIs | Slower response speeds at longer ISIs | N/A |

Next, the four heterogeneity types need to extract different EEG feature data for machine learning regression analysis to obtain four predicted index scores. The four heterogeneity types are weighted as follows (1)-(4):

Attention:

$$d'\text{+Omissions+Commissions+HRT+HRT SD+Variability} \quad (1)$$

Impulsivity:

$$\text{Commissions+Perseverations}-\text{HRT} \quad (2)$$

Sustained Attention:

HRT Block Change (if Omissions by Block|| Commissions by Block==1 then score+10) (if Omissions by Block && Commissions by Block==1 then score+20) (3)

Vigilance:

HRT ISI Change (if Omissions by ISI|| Commissions by ISI==1 then score+10 (if Omissions by ISI && Commissions by ISI==1 then score+20) (4)

The 4 predicted index scores may be respectively further classified into 5 levels according to severity, as shown in Table II, wherein the greater the score is, the more serious the symptom is.

TABLE II

| Predicted index scores | | | | | |
|---|---|---|---|---|---|
| Attention | <270 | 270~300 | 300~330 | 330~360 | >360 |
| Impulsivity | <40 | 40~50 | 50~60 | 60~70 | >70 |
| Sustained Attention | <40 | 40~50 | 50~60 | 60~70 | >70 |
| Vigilance | <45 | 45~50 | 50~55 | 55~60 | >60 |

The present invention has used the EEG data of 30 children with ADHD to establish a regression model, and finally calculated that the adjusted R-squared is greater than 0.6, which means that the regression model has a good degree of simulation, explanation and performance, and the EEG data of an additional 9 children who performed attention-related game tests were independently conducted to predict each heterogeneity score, and the prediction results are shown in FIG. 5. The results are shown in FIG. 5. In this way, a scientific, data-based approach can be provided to clinicians to aid diagnosis and to occupational therapists to provide appropriate treatment for patients with different symptomatology.

In summary, the present invention provides an early auxiliary diagnostic system for hyperactivity disorder, which learns and classifies the EEG signals of the subjects by machine, and calculates a predicted index score by using the test results of various tests together with the sign data of the brain porter, so as to further distinguish the type of ADHD and make the test results more convincing. In addition, the invention also records the resting EEG signals of the subject in the resting state and the working EEG signals of the subject during the test, and then classifies them to determine whether the subject is a normal person or not, and collects the data of the normal person as a benchmark to compare with the ADHD patient.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. An early assistive diagnosis system of attention deficit hyperactivity disorder (ADHD), comprising:

an attention testing device providing a test to a subject;

a brain-computer interface (BCI) including a plurality of electrodes and channels respectively corresponding to the electrodes, wherein the plurality of electrodes are configured to be arranged on a scalp of the subject to detect a plurality of electroencephalography (EEG) signals of the subject, wherein the plurality of EEG signals includes resting-state EEG signals detected during rest and task-state EEG signals during test; and a host connected to the attention testing device and the BCI to receive and analyze the plurality of EEG signals detected by the BCI, wherein the host includes:

a controller connected to the attention testing device receives and generates a plurality of test scores of the test;

a feature acquisition processor connected to the controller and the BCI acquires a plurality of ADHD-related features of the plurality of EEG signals of frequency band power of each of the channels on the plurality of electrodes and band ratio thereof, so as to obtain EEG feature data;

a first filter, which connected with the BCI and the feature acquisition processor, wherein the first filter is configured to receive the plurality of EEG signals, removes artifacts in the plurality of EEG signals, and preserves primary frequency range of EEG;

a second filter, which connected to the BCI and the first filter, wherein the second filter is configured to remove artifacts originating from eye or muscle movements within the plurality of EEG signals using an artificial-intelligence algorithm;

a time-frequency converter, which connected to the BCI and the second filter, wherein the time-frequency converter is configured to transform time-domain signals of the resting-state EEG signals and the task-state EEG signals into frequency-domain signals, subsequently computing the frequency band power of each frequency band of each channel; and a feature analysis processor connected to the feature acquisition processor receives the EEG feature data, classifies the subject as typical development group or ADHD group according to the EEG feature data, and when the subject is classified as ADHD, the feature analysis processor combines the EEG feature data and the test scores corresponding to the subject to produce predicted index score ranges of a plurality of ADHD heterogeneity types.

2. The early assistive diagnosis system of ADHD according to claim 1, wherein the channels respectively having different frequency band powers.

3. The early assistive diagnosis system for ADHD according to claim 1, wherein the feature analysis processor uses a machine learning algorithm to classify the subject.

4. The early assistive diagnosis system for ADHD according to claim 1, wherein the feature analysis processor uses machine learning algorithms to compute the ADHD heterogeneity types of the subject.

5. The early assistive diagnosis system for ADHD according to claim 4, wherein the machine learning algorithm is a regression analysis.

6. The early assistive diagnosis system of ADHD according to claim 1, wherein the ADHD heterogeneity types include problems of attention, impulsivity, sustained attention, and vigilance.

7. The early assistive diagnosis system of ADHD according to claim 1, wherein the attention testing device is a computer, and the test is a game-based or video-based stimulating vision or audition for the subject.

8. The early assistive diagnosis system for ADHD according to claim 1, wherein when a new subject undergoes the test and EEG signals are measured, the feature acquisition processor obtains the EEG feature data of the new subject to predict an index score, and by comparing when the index score of the new subject falls within the predicted index score range, the feature analysis processor determines the ADHD heterogeneity types of the new subject.

* * * * *